(12) United States Patent
Kudla et al.

(10) Patent No.: US 9,018,007 B2
(45) Date of Patent: Apr. 28, 2015

(54) METHOD AND DEVICE FOR CELL CULTURE IN OPEN CONTINUOUS MODE

(75) Inventors: Bernard Kudla, Les Molieres (FR); Pierre-Yves Chesneau, Villebon-sur-Yvette (FR); Yann Beaujouan, Nanterre (FR)

(73) Assignee: Metabolium, Romainville (FR)

( * ) Notice: Subject to any disclaimer, the term of this patent is extended or adjusted under 35 U.S.C. 154(b) by 455 days.

(21) Appl. No.: 12/918,987

(22) PCT Filed: Feb. 20, 2009

(86) PCT No.: PCT/FR2009/050275
§ 371 (c)(1),
(2), (4) Date: Aug. 23, 2010

(87) PCT Pub. No.: WO2009/112739
PCT Pub. Date: Sep. 17, 2009

(65) Prior Publication Data
US 2011/0003390 A1 Jan. 6, 2011

(30) Foreign Application Priority Data
Feb. 21, 2008 (FR) ...................... 08 51123

(51) Int. Cl.
*C12N 5/02* (2006.01)
*C12M 1/00* (2006.01)

(52) U.S. Cl.
CPC .................... *C12M 47/04* (2013.01)

(58) Field of Classification Search
CPC .................................... C12M 47/04
See application file for complete search history.

(56) References Cited

U.S. PATENT DOCUMENTS

| 6,686,194 B1 * | 2/2004 | Mutzel et al. ............ 435/286.5 |
| 2006/0257999 A1 * | 11/2006 | Chang et al. ............ 435/289.1 |
| 2007/0031963 A1 * | 2/2007 | Chang et al. ............ 435/304.3 |
| 2007/0037276 A1 | 2/2007 | De Crecy |
| 2008/0220501 A1 | 9/2008 | De Crecy |

FOREIGN PATENT DOCUMENTS

| WO | WO0034433 A1 | 6/2000 |
| WO | WO2005083052 A1 | 9/2005 |

OTHER PUBLICATIONS

Bavister et al., A minichamber device for maintaining a constant carbon dioxide in air atmosphere during prolonged culture of cells on the stage of an inverted microscope, 1988, in Vitro Cellular & Developmental Biology, vol. 24, No. 8, 759-763.*
Ragout et al., Selection of an adhesive phenotype of *Streptococcus salivarius* subsp. thermophilus for use in fixed-bed reactors, 1996, Appl. Microbiol. Biotechnol. 46(2): 126-31.*
Keevil, Continuous culture models to study pathogens in biofilms, 2001, Methods in Enzymology: Microbial Growth in Biofilms Part B, (337): 104-122.*
Favero et al., Use of Laminar Air-Flow Equipment in Microbiology, 1968, Appl. Microbiol. 16(1): 182-183.*
Crecy-Lagard et al., Long term adaptation of a microbial population to a permanent metabolic constraint: overcoming thymineless death by experimental evolution of *Escherichia coli*, 2001, BMC Biotechnol. 1:10.*

* cited by examiner

*Primary Examiner* — Robert Yamasaki
(74) *Attorney, Agent, or Firm* — Browdy and Neimark, PLLC

(57) ABSTRACT

The present invention relates to the use of cell cultures in the open continuous mode, to a method for selecting static cell variants or cell variants which proliferate in suspension, to a culture substrate and to a device suitable for implementing this method.

18 Claims, 10 Drawing Sheets

METHOD AND DEVICE FOR CELL CULTURE IN OPEN CONTINUOUS MODE

The present application relates to the implementation of cell cultures in open continuous mode.

When carrying out cell cultures, a distinction is conventionally drawn between batch culture methods and continuous culture methods.

In the batch culture techniques, culture vessels containing a sterile growth medium are seeded with a fraction of a culture which has previously developed in a mother culture. In order to be able to reproduce the same characteristics, the daughter culture is generally seeded at a given dilution, then it is induced to complete a growth cycle similar to that of the mother culture. In the case of industrial fermentations, it is useful to reproduce the same culture conditions for each cycle initiated as this makes it possible to predict beforehand the moment when the cultures reach completion, or achieve a growth stage favourable to the recovery of a product of interest synthesized or transformed by the cells.

In the field of research, reproducibility between daughter cultures is necessary in order to obtain reliable and representative experimental data. In order to obtain this reproducibility, a synthetic culture medium, identical culture supports and standardized culture conditions are commonly used. The cultures are then placed in closed vessels under sterile conditions, in an incubator under constant temperature and pressure.

This reproducibility can also be increased by the use of automated incubators making it possible, for example, to seed the cultures in synchronous manner using a robotic arm. This type of incubator can take the form of a closed container inside which the temperature and the pressure are finely regulated. Once the vessels are seeded they are closed and placed in culture for a specific period of time.

In a cycle of batch culture in liquid medium, it is known that the cells develop by passing through different successive stages of growth. These different stages of growth correspond to distinct physiological states, which are a function of changes in the composition of the culture medium over time. In general, while there are few cells in the culture medium, these exploit the carbonaceous substrates which are easiest to assimilate and favour a growth metabolism inducing them to divide actively. When said substrates are depleted, the cells start hydrolyzing more complex substrates using more specific enzymes, and activating more complex metabolic pathways allowing their assimilation. They then enter into a subsistence strategy. It is often at this stage that the cells synthesize reserve products, enzymes and antibiotics, some of which are of industrial interest. On completion of the culture cycle, when the medium is depleted, many cells die whilst others resist in the form of biofilms, spores, or any other quiescent form specific to the cell species concerned.

In batch mode, it is possible, for a given culture medium and cell type, to define, on the basis of fundamental physicochemical parameters such as cell density, pH, oxygen, carbon or nitrogen levels, or any other parameter indicative of the growth stage of the cells, the growth stage at which the vast majority of the cells are to be found at a given moment. In fact, if the culture medium is homogeneous, the development of all of the cells is relatively synchronous. It is then possible to associate, for example, a cell density value with a more or less rapid phase of growth of the cells, in particular via the use of a standard growth curve. It is also possible to carry out direct observations with a microscope in order to determine the growth stage based on morphological criteria.

Experiments consisting of reproducing the same culture cycle in batch mode a very large number of times in succession, have been described in the literature. These experiments show that it is possible to reproduce cells over very long periods without altering the characteristics or the properties of the cells (Lenski, R. E. and Travisano, M. (1994): Dynamics of adaption and diversification: A 10 000-generation experiment with bacterial populations, Proc. Natl. Acad. Sci. USA 91, 6808-6814).

In the continuous culture techniques, by contrast, the culture benefits from a regular supply of fresh culture medium or diluent, i.e. a component of said culture medium, so as to maintain the growth of the cells over a long period. The dilution of the medium is generally carried out according to a preselected regime, which can be periodic or continuous.

The following are identified as the main systems of continuous culture, a mode where fresh medium is added so as to keep the cell density constant around an average value (turbidostat mode) and a mode where fresh medium, or a diluent, is introduced so as to keep a physicochemical parameter (pH, C/N ratio etc.) around a defined value (chemostat mode).

Paradoxically, the attempts described in the literature to maintain continuous cultures over very long periods, have not made it possible to maintain cell lines for as long as when using batch culture techniques (Dijkuizen, D. E. (1993: Chemostats used for studying natural selection and adaptive evolution. Meth. Enzymol. 224, 613-631). This finding can be explained by the fact that, in continuous mode, the cells reach different physiological stages fairly rapidly and are not all at the same growth stage. Without doubt, the regular supply of fresh medium further disturbs the micro-environment of the cells and does not make it possible to obtain a completely homogeneous culture medium. Thus, after a certain number of generations, there is a systematic appearance of static cell variants referred to as having "resistance to dilution". These variants occur in the form of biofilms, filaments or quiescent forms (spores, cocci, etc.). They form a sub-population which escapes the constraints of adaption and sometimes the selection agents (antibiotics or others) used in the culture medium. All the continuous mode culture equipment described promotes the appearance of static variants. These variants occupy the inner surfaces of the equipment and limit its efficiency (Chao, L. and Ramsdell, G. (1985): The effects of wall populations on coexistence of bacteria in the liquid phase of chemostat cultures. J. Gen, Microbiol. 131, 1229-1236). The continuous cultures with a constant concentration of cells (turbidostat mode), are particularly sensitive to invasion by variants which are resistant to dilution. Therefore they can only be carried out over relatively short periods generally allowing fewer than 200 generations.

Moreover, the cultures in continuous mode carried out under the conditions where the speed of cell growth is high promote spontaneous mutations in larger numbers.

These conditions prove to be particularly conducive to the development of adherent variants developing into biofilms, which are insensitive to dilution.

Due to these various difficulties, the continuous culture methods and devices disclosed in the literature are seldom used for industrial and even scientific purposes.

Their potential was however recognized very early (Monod, J. (1950): La technique de la culture continue. Theorie et applications, Ann. Inst. Pasteur 79, 390-410; Novick, A. and Szilard, L. (1950): description of the chemostat, science 112, 715-716).

However, the continuous culture techniques are now unexpectedly experiencing renewed interest, precisely due to the fact that they promote the emergence and selection of cell variants with differentiated growth. It may thus be desirable to obtain cell variants proliferating in suspension or, by contrast, static cell variants. The latter are particularly useful for studying, for example, the biology of biofilms.

The principle of this selection is to take advantage of the spontaneous changes promoted by the cultures in continuous mode, in order to select, over the long term, cell variants which preferentially develop in suspension, or by contrast essentially in static forms.

Whether or not they result from genetic mutations, the variants proliferating in suspension generally have a tendency to divide more actively than the other cells present in the medium, or to take greater advantage of the resources of the medium. If the culture is maintained over a long period, the frequency of these variants within the population increases over time, which makes it possible to isolate them more easily.

The variants proliferating in suspension selected according to this principle, generally have a competitive advantage over the other cells originating from the same line. They are therefore useful for improving, for example, the yield of existing industrial fermentation processes, such as those used in batch culture mode.

International application WO 00/34433 describes a device for the implementation of continuous cultures allowing the selection of variants proliferating in suspension. This device is equipped with two culture vessels connected to each other by a conduit which makes it possible to transfer a culture contained in a first vessel to a second and vice-versa at will. This conduit is provided with a valve that is actuated at will in order to pass the culture from one vessel to the other. Each of the two culture vessels is fed by an independent fluidic system allowing constant replenishment of medium and gas inside each of the vessels. A second fluidic system branches off from this fairly complex fluidic system, making it possible to clean and sterilize each of the two culture vessels independently, using sterilizing fluids. Said device is thus designed in order to be able to transfer a culture in liquid medium from a first vessel to a second. When one of the vessels contains the culture, the other can be cleaned and sterilized and vice-versa. During the sterilization and cleaning, the static variants adhering to the walls of the vessel are removed, whilst the cells proliferating in suspension are maintained in continuous culture in the other vessel. The device is designed to repeat the operation as many times as necessary. It is thus theoretically possible to maintain a continuous culture over an unlimited period while avoiding the accumulation of static variants.

However, on a practical level, this device has several major drawbacks, including in particular the following:

The cleaning and sterilization of the vessels within the device require a complex fluidic system. This fluidic system must be completely closed in order to maintain an appropriate level of sterility. Now, it is difficult to reproduce such a fluidic system on an industrial scale, because when the volume of the culture vessels is increased, the volume of sterilization and washing liquids necessary for the operation of the system becomes too great. These fluids must be stored while waiting to be decontaminated, which results in high maintenance costs. Moreover, the operation of the system requires the involvement of two vessels for an effective selective culture. These elements limit the number of cultures which can be implemented on the same technical platform.

Access to the cells in culture is difficult due to the fact that the cultures are maintained in a closed vessel. This access is further reduced to the extent that the sterility of the fluidic system must be ensured. It is therefore difficult to monitor the cultures, in particular in real time.

The introduction into the culture of insoluble, immiscible substances or solutions that are miscible with the medium used with difficulty, is also complicated by the need to make use of the fluidic system and to ensure the containment of the cultures.

The pressure between the different compartments of the device is difficult to regulate, which makes a constant and homogeneous pressure within the system practically impossible. Under these conditions the reproducibility of the cultures is affected. Moreover, excess pressures can occur in the fluidic system and thus disturb or interrupt the operation of the device;

The transfer of the culture from one culture vessel to the other does not make it possible to carry out cultures in static mode as it necessarily involves putting the cells back in suspension and removing the static variants.

International application WO 2005/083052 describes another device for the selection of variants proliferating in suspension in continuous culture. This device takes the form of a flexible tube, inside which the culture is produced between two clamping points situated upstream and downstream of the tube. The replenishment of the culture medium is carried out by supplying fresh medium and removing the same volume of the used medium by moving the tube between the clamping points. The opening and closing of the clamping points create a peristaltic effect. The new segments of tube introduced between the clamping points supply the fresh medium and participate in the dilution, whilst the static mutants which adhere to the walls, are removed as the tube moves to the level of the used segments of the latter.

This device has the same limitations as the previous one as regards the volume and containment of the culture. Moreover, it appears difficult to suitably ensure gaseous exchanges by diffusion through the single wall of the tube.

The objective of the method and the device according to the present invention is to remedy the limitations of the culture devices described above.

One of the objectives of this invention is to make it possible to continuously culture cell cultures in order, in particular, to select variants at a specific growth stage. According to the invention, these cultures are carried out on culture supports and in culture vessels in open mode, placed in a closed container.

By culture vessel or culture container is meant according to the invention a culture medium container, generally intended to be placed in direct contact with the culture medium. By culture support is meant according to the invention an assembly comprising a culture vessel and a support for the culture vessel. The culture support described hereafter according to the invention is a particular culture support.

The particular structure of the continuous cell culture method described hereafter, irrespective of the culture vessel or culture vessels used and placed inside the closed container used in this method, allows easier access to the cultures carried out in continuous mode.

The particular structure of the culture supports according to the invention described hereafter, placed inside the container of the device according to the invention, allows easier access to the cultures carried out in continuous mode. These culture supports are designed so that the culture vessels that they contain can be replaced at will, for example according to a preferred aspect of the invention when the cultures accumulate too great a number of static variants. But other culture supports and/or culture vessels can also be envisaged within the context of the present invention, and used within the method according to the invention.

Handling operations inside the closed container can be carried out using robotic manipulating arms, which, moreover, considerably reduces the risks of contamination.

According to the invention, the number of culture supports and/or culture vessels present in the device can be adapted by simple dimensioning of the closed container where they are placed. It is therefore possible to implement several cultures at the same time, in series or in parallel.

The method and the device, as well as the method for utilization of this device, described in the present application, have numerous advantages, among which there may be mentioned:

- The possibility of culturing uni- or oligo-cellular organisms in suspension (aerobic or anaerobic depending on the gas mixture present inside the closed container), at a homogeneous temperature and pressure, in a liquid phase, under sterile conditions. In particular that of culturing photosynthetic microorganisms which require constant lighting and a culture in suspension mode, without stirring;
- The possibility of carrying out continuous cultures over a large number of generations with a constant volume, to a growth stage of the cells defined as a function of a predefined physicochemical parameter measured directly in the culture (cell density, pH, concentration of a product etc.) over a period which can be very long.
- The possibility of measuring the different parameters necessary for the on-line control or monitoring of the culture (pH, pO2, substrates, products etc.).
- The possibility of applying to the culture physicochemical parameters creating a selection pressure and which can be modified (supplies of molecules, T° C., pH, etc.)
- The possibility of separating, as frequently as necessary, the biomass in suspensive growth (subject to dilution) from the biomass immobilized on any wall of the culture system (insensitive to the dilution), by pipetting and transfer of the culture into a new sterile culture vessel and/or replacement of the culture support.
- The possibility of selecting static variants (instead of the variants proliferating in suspension) by removal of the liquid phase present in the vessels and/or culture supports and replacement of this liquid phase by a fresh medium by, for example, resuspending the static variants adhering to the support.
- The possibility of making use of single-use, disposable or recyclable culture supports and/or culture vessels and/or pipetting equipment.

A subject of the present invention is a method for cell culture in generally open continuous mode, allowing in particular the selection of cell variants proliferating in suspension or in a static manner.

By culture in continuous mode, or continuous culture, is meant according to the invention a culture carried out in a liquid medium in which a fraction of said culture medium is replenished with a view to maintaining the cells in growth in a prolonged manner. Preferably, the cells are maintained over a large number of generations which is not defined beforehand, preferably greater than 100 generations, more preferentially 200, even more preferentially 1000 generations.

The replenishment of the culture medium, or of a component of the latter (diluent), can be constant, regular or periodical. The culture medium can be replenished for one or more of the ingredients included in its composition, or for the whole mixture of these ingredients. The culture medium is generally replenished so that at least a majority of cells, preferably at least 50% of the cells in culture, more preferentially at least 80% thereof are maintained in suspension.

According to the invention, the culture medium is more generally a liquid culture medium.

Hereafter the terms "culture medium" and "culture" are used interchangeably.

A "cell" is here defined as a small biological entity comprising a cytoplasm delimited by a membrane and having the ability to reproduce autonomously. The cell can be eukaryotic or prokaryotic, animal or plant. Microorganisms are considered as cells.

Bacteria, yeasts and unicellular algae are cells preferred for the implementation of the present invention.

By liquid culture medium is meant a liquid mixture comprising nutrients, as well as optionally other components such as selection agents (antibiotics), in which cells can multiply.

A cell variant is defined as a daughter cell not having the same physiological characteristics as its mother cell cultured under the same conditions.

The variant can be subjected to physiological changes, which can arise because of a genetic change (point mutation, loss or acquisition of genetic material), but can also result from stress or any other factor which can have a lasting effect on the behaviour of the cells in culture.

It is not required according to the invention that these physiological changes be predefined. On the contrary, the invention has the objective of promoting the emergence of cell variants from spontaneous changes then selecting from these variants those which have acquired properties endowing them with a competitive advantage over the other cells in culture. In general, these new properties allow them to multiply more rapidly or to make better use of the culture medium.

The cell variants according to the invention can be selected according to two main modes:

- variants in suspension: the variants which are more competitive in a planktonic development in liquid culture are selected. In this case, it is the static variants which it is sought to remove.
- static variants: the variants which bind, aggregate, become encysted or take any other form of resistance to the dilution, for example in the form of biofilms, are selected. In this case, it is the variants which develop in suspension that it is sought to remove.

The continuous cell culture method allowing the selection of cell variants that are static or proliferating in suspension according to the invention is characterized in that it comprises one or more of the following stages, more generally the following stages, whereby:

a) a liquid culture medium contained in a first culture vessel kept open in a closed container is seeded using one or more live cells, b) said cells, in said culture medium, are brought to a specific growth stage, corresponding to a given cell density or to a physicochemical parameter measured in the culture medium, c) the cell density in the culture medium, or the value of said physicochemical parameter, reached in stage b), is kept substantially constant by supplying fresh culture medium or at least one diluent in said culture vessel, d) a portion of the culture medium obtained in c) containing the cells in suspension is removed by pipetting so as to maintain the volume of the culture;

e) a fraction of the culture medium obtained in d) is transferred into a second culture vessel, which generally replaces the first culture vessel;

f) said first culture vessel with the remaining culture fraction that it contains is withdrawn or even removed;

g) after several generations of culture in the second vessel, the cells proliferating in suspension and/or the static cell variants are selected.

In stage c) according to the invention, whether for the above method according to the invention or for one of the methods according to the invention described hereafter, it is not excluded that the supply of fresh culture medium or at least one diluent in said culture vessel is also a simultaneous supply of fresh culture medium and at least one diluent. In general, by at least one diluent, a (single) diluent is preferred, but it is possible to use several diluents without exceeding the scope of the invention.

According to the invention, all the culture vessels present in the closed container are generally identical, but it is possible for the culture vessels to be different from each other, or to be of several different types within the same container.

According to this method, it is possible to select, separately or simultaneously, cell variants proliferating in suspension as well as static variants.

When it is more particularly desired to select variants proliferating in suspension, the following procedure may more particularly be followed. A method according to the invention of continuous cell culture allowing the selection of cell variants proliferating in suspension, can be characterized in that it comprises the following stages:

a) a liquid culture medium contained in a first culture vessel kept open in a closed container is seeded using one or more live cells, b) said cells, in said culture medium, are brought to a specific growth stage, corresponding to a given cell density or to a physicochemical parameter measured in the culture medium, c) the cell density of the culture, or the value of said physicochemical parameter, reached in stage b), is kept substantially constant in said culture vessel by supplying fresh culture medium or at least one diluent, d) a portion of the culture medium containing the cells in suspension is removed by pipetting so as to maintain the volume of the culture;

e) a fraction of the culture obtained in d) in which the cells are in suspension, is transferred to a second culture vessel replacing the first;

f) said first culture vessel with the remaining culture fraction that it contains is withdrawn;

g) after several generations of culture in the second vessel, the cells proliferating in suspension are selected.

According to this aspect, the fraction of the culture removed with the vessel in stage f) is generally made up of static variants. Stage f) is a withdrawal stage, or a removal stage, or a withdrawal or removal stage.

When it is more particularly desired to select static variants, the following procedure may be followed:

a) a liquid culture medium contained in a first culture vessel is seeded using one or more live cells, in which at least one solid surface, preferably a plate, is placed, said vessel being kept open in a closed container, b) the cells, in the seeded culture medium, are brought to a specific growth stage, corresponding to a given cell density or to a physicochemical parameter measured in the culture, c) the cell density of the culture, or the value of said physicochemical parameter, reached in stage b), is kept substantially constant by supplying fresh culture medium or at least one diluent in said culture vessel, d) a portion of the culture medium obtained in c) containing the cells in suspension is removed by pipetting so as to maintain the volume of the culture;

e) said solid surface on which a fraction of the culture obtained in d) is deposited, is transferred to a second culture vessel replacing the first;

f) said first culture vessel with the remaining fraction of culture that it contains is withdrawn;

g) after several generations of culture the static cell variants adhering to said solid surface are selected.

According to this aspect of the invention, the fraction of the culture removed with the vessel in stage f) most often corresponds to a liquid fraction in which most of the cells proliferating in suspension are present. Stage f) is a withdrawal stage, or a removal stage, or a withdrawal or removal stage.

This embodiment of the invention more particularly involves solid surfaces. These solid surfaces offer the possibility for static cell variants to adhere during the selection process. The solid surfaces can take different forms such as plates, beads or particles. They can be made of different inorganic or organic materials (plastics, metals, glasses, minerals, composites). The plastic materials such as polystyrene, polycarbonate, polyethylene, polypropylene, polyurethane and their derivatives are preferred. The surfaces can be treated physically or chemically. They can be placed in suspension in the culture medium, attached to or placed in the bottom of the culture vessel. Preferably, the solid surfaces are designed to be withdrawn through the opening of the culture vessel, and placed in a new culture vessel containing, for example, fresh medium.

According to a preferred embodiment of the method, said solid surface is made up of a material treated in order to avoid adherence of the cells. In fact, the method can comprise a stage during which different surfaces are tested in order to determine which of these surfaces allows a better or lesser adhesion of the static variants. In this, the method can be particularly useful for the selection of material limiting the adhesion of the cells with a view to developing, for example, surgical equipment such as catheters limiting contaminations. Conversely, this method can be useful for selecting materials promoting the installation of the sought cells (biogenic surfaces) in the development of prostheses or medical implants.

The method according to the invention advantageously allows the selection of cell variants at a predefined growth stage.

In fact, according to stage b) of said method, the cells in the culture medium are preferentially brought to a growth stage, which is determined by or linked to the cell density or to a measurable physicochemical parameter in the culture medium such as the pH, the dissolved amount of oxygen, carbon or nitrogen available, etc. . . .

In order to arrive at this "specific" growth stage it is possible to proceed on the basis of standard growth curves, established beforehand, experimentally or from data in the literature. These curves are generally established on the basis of cultures carried out in batch mode. They make it possible to link the cell density or a physicochemical parameter of the culture medium to the physiological state in which the majority of the cells in culture are to be found at a given moment.

It is known to a person skilled in the art that, during a culture cycle cells pass through different physiological states linked in particular to the depletion of certain substrates in the culture medium, in particular when the culture medium is not replenished. These physiological states generally reflect an adaptation of the cells to their environment.

According to a preferred aspect of the invention, a particular measurable value of a physicochemical parameter is set, for example, a cell density value known to be a parameter determining the secretion of an enzyme of interest. The method provides that after seeding of the culture medium, the cells develop until they reach the set value. When this critical value is reached, the culture in continuous mode is initiated so as, for example, to keep the cell density constant. It is thus possible to keep the cells in the desired physiological state for as long as possible, which makes it possible, for example, to prolong the period during which the cell will secrete the product of interest.

According to the invention, the cell cultures are generally carried out in open mode, which facilitates interventions and removal of samples requiring the chosen physicochemical parameters to be maintained at a constant value. This means that the culture vessels chosen to implement the method most often have an opening that is sufficiently wide and practical, preferably oriented upwards or towards the top, in order to advantageously introduce the equipment necessary to take samples of the culture medium by pipetting, or to carry out direct measurements using probes. By top is generally meant the highest point of the culture vessel, with respect to a horizontal base which can be the floor.

Thus, according to a preferred embodiment of the invention, the method is characterized in that said culture vessels are kept open at the top, and that a stream of gas, such as sterile air, is applied continuously at the periphery of their opening.

In this, the present method differs from methods of culture in continuous or semi-continuous mode described in the prior art, which are carried out in closed vessels, which do not make it possible to establish monitoring of the cultures in real time.

The method according to the invention therefore makes it possible to make a selection of cell variants maintained, or even synchronized, at a predefined growth stage. This is particularly useful for selecting, for example, cell variants which synthesize products of interest such as enzymes or antibiotics in a transient manner. The selection of the cell variants can thus be implemented by reproducing the conditions in which the cells synthesize the product of interest. The method according to the invention is therefore particularly suited to the improvement of industrial strains used in fermentation processes, in particular those used in semi-continuous mode (i.e. those during which the culture medium is replenished over a set period of time).

A particular aspect of the invention consists, independently of the selection of variants in suspension or static variants, in the implementation of the method described previously for synthesizing a product of interest over an unlimited period, by maintaining the cells at an optimum growth stage for the synthesis of said product.

The method according to the invention is generally implemented in a closed container, the size of which can vary depending on the needs of users, the number and the volume of the cultures.

More particularly, according to an embodiment of the invention, different stages a) to f) are carried out in a closed container.

The pressure and the temperature can be kept constant in the container at the desired values. The culture vessels being open, the cultures are generally at the same pressure as that applied in the container. The risks of local excess pressure encountered in the contained systems of the prior art are thus generally discarded.

Said container also makes it possible to control the gaseous environment of the cultures, which is particularly useful in case of a culture carried out under anaerobic conditions.

The culture method most often provides that sterile gases, such as sterile air, is injected under pressure into the culture medium of the cells by means of a bubbling device, for example in the form of aeration rods introduced into the culture vessel generally through the opening of said vessel. This injection of gas allows the aeration of the culture medium, the homogenization of said medium by air lift (stirring by bubbling) and contributes to the maintaining of a certain pressure of gas inside the container.

According to the method, a sterile gas stream preferentially passes through the container. This stream can be constituted by a gas, such as nitrogen or a mixture of gases such as air, depending on the chosen culture conditions. Preferably, the sterile gas stream is applied at the periphery of the opening of the open culture vessels in order to remove the contaminants from this zone and therefore reduce the risks of contamination. This stream also makes it possible to balance the pressure inside the container.

The conditions of circulation of the sterile gas stream are most often identical for all the vessels in the closed container.

For a greater efficiency of the system, the gas stream, which is preferably a laminar stream, is generally applied either from the top to the bottom of the culture vessels, or from the bottom to the top of the culture vessels, generally to the outside of said culture vessels. The device according to the invention described hereafter is a device in which the sterile gas stream is applied (or directed) from the top to the bottom of the culture vessels.

More preferentially, the gas stream is activated at the periphery of the culture vessels, in particular around the opening of said vessels, by creating a partial vacuum at the bottom of the culture vessels. In order to obtain this partial vacuum locally the culture vessel can be placed in a containment tank which is open towards the top and provided at its base with means for aspirating and discharging the gas stream. A partial vacuum can be then obtained locally in the volume situated between the culture vessel and the internal walls of said containment tank.

Preferably, the sterile air passes from the top to the bottom in the volume situated between the internal walls of the containment tank and the culture vessel, and it is discharged out of the container at the bottom of the culture vessels. In this way the contaminants are trapped in said volume and carried along towards the bottom of the containment tank. Thus, they do not get inside the culture vessel, which is under slight excess pressure, due in particular to the supply of gas produced by bubbling in the culture medium.

Another embodiment would comprise the activation of the sterile gas stream from the bottom to the top of the culture vessels.

According to a preferred embodiment of the invention, several cultures are carried out simultaneously in several culture supports placed in the same container. By several, is meant at least two.

The sterile gas stream is particularly useful for avoiding cross-contaminations when different cultures are carried out simultaneously in the same container.

According to a preferred aspect of the method described above, stages a) to f) above are reiterated one or more times before proceeding with stage g).

According to an embodiment of the invention, a substantially constant cell density is maintained in the culture in stage c) by diluting the culture with fresh medium keeping a constant volume of culture medium in the culture vessel.

In the case of a selection of variants in suspension, the transfer of the culture medium containing the cells in suspension to the second culture vessel can be carried out by pipetting using a sterile pipette. The pipetting operation is preferably carried out using a robotic arm situated inside the closed container.

The first used culture vessel is generally withdrawn from the culture support to which it may belong. In all cases, this first culture vessel is removed from the closed container using an airlock. This airlock makes it possible to keep the pressure and sterility inside the container stable. The removed vessel is generally discarded.

The culture vessel in operation can be placed in a thermostatically controlled cell, i.e. in an open container the walls of which are maintained at the desired temperature, allowing regulation of the temperature of the cell culture. According to a preferred aspect, the containment tank is itself thermostatically controlled and serves as a cell. One of the walls of the tank can, in fact, comprise a means for heating allowing the regulation of the temperature of the objects placed in the internal volume of said tank. In the case of the presence of a thermostatically controlled cell around the culture vessel, the space between the culture vessel and the internal walls of the containment tank must of course be understood as the space between the thermostatically controlled case and the containment tank.

The culture supports and/or the culture vessels according to the invention are preferentially single-use and are compatible with robotic handling inside the container. In fact, the invention preferably provides that at least some, i.e. several, stages of the method are carried out using one or more automated arms allowing movements inside the container. Preferably the container remains closed during the different stages of the method.

According to the invention the cells are generally cultured continuously over a number of generations greater than $10^2$, preferably greater than $10^4$, more preferentially greater than $10^6$, and even more preferentially greater than $10^{10}$ generations, without (direct) opening of the container to the outside environment.

Preferably, the culture method according to the invention in the open continuous mode is implemented using a culture device particularly suited to this purpose.

The invention also relates to a culture support making it possible to carry out a cell culture in open continuous mode, characterized in that it comprises:
  at least one culture vessel open at the top suitable for containing a liquid culture medium;
  at least one containment tank open towards the top, in which said culture vessel is housed;
  a space between said culture vessel and said containment tank, suitable for allowing a gas stream to circulate at the periphery of the opening of the vessel, from the top to the bottom, between the culture vessel and the internal walls of the containment tank; and
  a means for extracting said gas stream, situated in the lower part of the containment tank.

Preferably, the means for extracting the gas stream consists of one or more openings allowing passage of the gas stream, for example air.

In an embodiment, the culture support is presented in the form of a removable block in which several of said containment tanks are grouped together and in which at least one of said culture vessels is housed.

In preferred manner, said lower part of the containment tank is embedded in a base provided with additional means for extracting said gas stream circulating between the culture vessels and the walls of the containment tanks, such as a pipe connected to a vacuum pump, or one or more gas distribution means.

The culture support according to the invention can comprise at least one means for regulating the temperature of the internal volume of said containment tank, said means for regulating the temperature of the internal volume of said containment tank preferably consisting of a heating resistance enclosed in at least one of the walls of said containment tank.

The culture support according to the invention can comprise at least at least one means for injecting air into the culture medium (media), contained in said vessel(s), such as one or more aeration rods.

The culture support according to the invention can comprise at least one means for optically measuring the cell density present in the culture medium contained by the culture vessel.

The culture support according to the invention can comprise at least one means for producing light for the culture of microorganisms in autotrophic mode, situated in the space between the culture vessel and the inner walls of said containment tank, or enclosed in one of the walls of said containment tank.

The invention finally relates to a cell culture device allowing a continuous growth of the cells in open mode, characterized in that it comprises:
  a container;
  a means for generating a sterile gas stream passing through said container;
  one or more culture supports according to the invention as described previously, positioned in said container, making it possible to carry out a cell culture in open mode.

The cell culture device can comprise at least one means for replenishing the culture medium placed inside said container.

The cell culture device can comprise at least one culture vessel suitable for replacing that contained in the culture support.

The cell culture device can be characterized in that the means for generating the sterile gas stream is placed in the upper part of the container so that said sterile gas stream is directed from the top to the bottom of the culture support.

The cell culture device can moreover comprise at least one means for extracting the sterile gas stream at the base of said culture vessel, said means for extracting the sterile gas stream preferably creating a partial vacuum in the space situated between the culture vessel and the containment tank of the culture support. Said means for extracting can be associated with at least one means for aspirating the air suitable for extracting the air surrounding the periphery of the opening of the culture vessel.

The cell culture device can be characterized in that the means for replenishing the culture medium comprises a means for transferring part of the contents of the culture vessel to a discharge zone.

The cell culture device can be characterized in that the means for replenishing of the culture medium comprises a means for transferring fresh medium from a reserve situated inside the container to the culture vessel.

The means for transferring preferably comprises a pipette and a means for aspirating the fresh or used medium in said pipette.

The cell culture device can, moreover, comprise at least one outlet means to the outside of the container of the means for transferring and/or at least one culture vessel, said outlet means preferably comprising an airlock.

The cell culture device can be characterized in that it comprises at least one means for injecting air into the culture.

The cell culture device can be characterized in that it comprises at least one automated arm suitable for carrying out movements inside the container.

The cell culture device can be characterized in that the container is closed.

The cell culture device can comprise several culture supports positioned in said container, for carrying out several cell cultures in open mode in parallel.

The cell culture device can be characterized in that it allows the implementation of the method according to the invention.

The invention will be better understood on reading the following figures, in which:

FIG. 1 diagrammatically represents a first culture support according to the invention, in perspective;

FIG. 2 diagrammatically represents a second culture support according to the invention, in perspective;

FIG. 3 diagrammatically represents a removable block comprising cells for culture supports as shown in FIG. 2, in section III-III with respect to FIG. 4;

Figure 6:
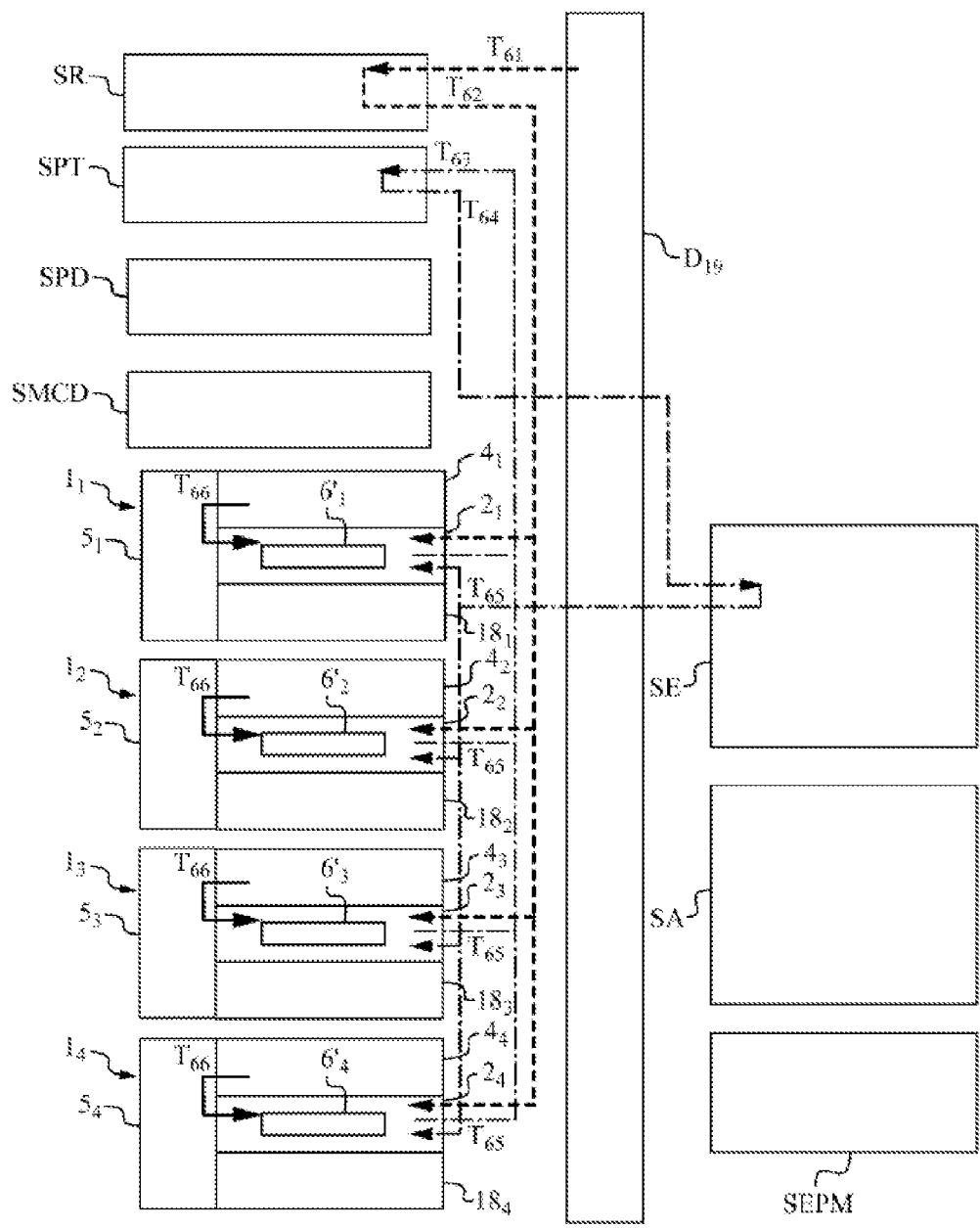
Figure 7:
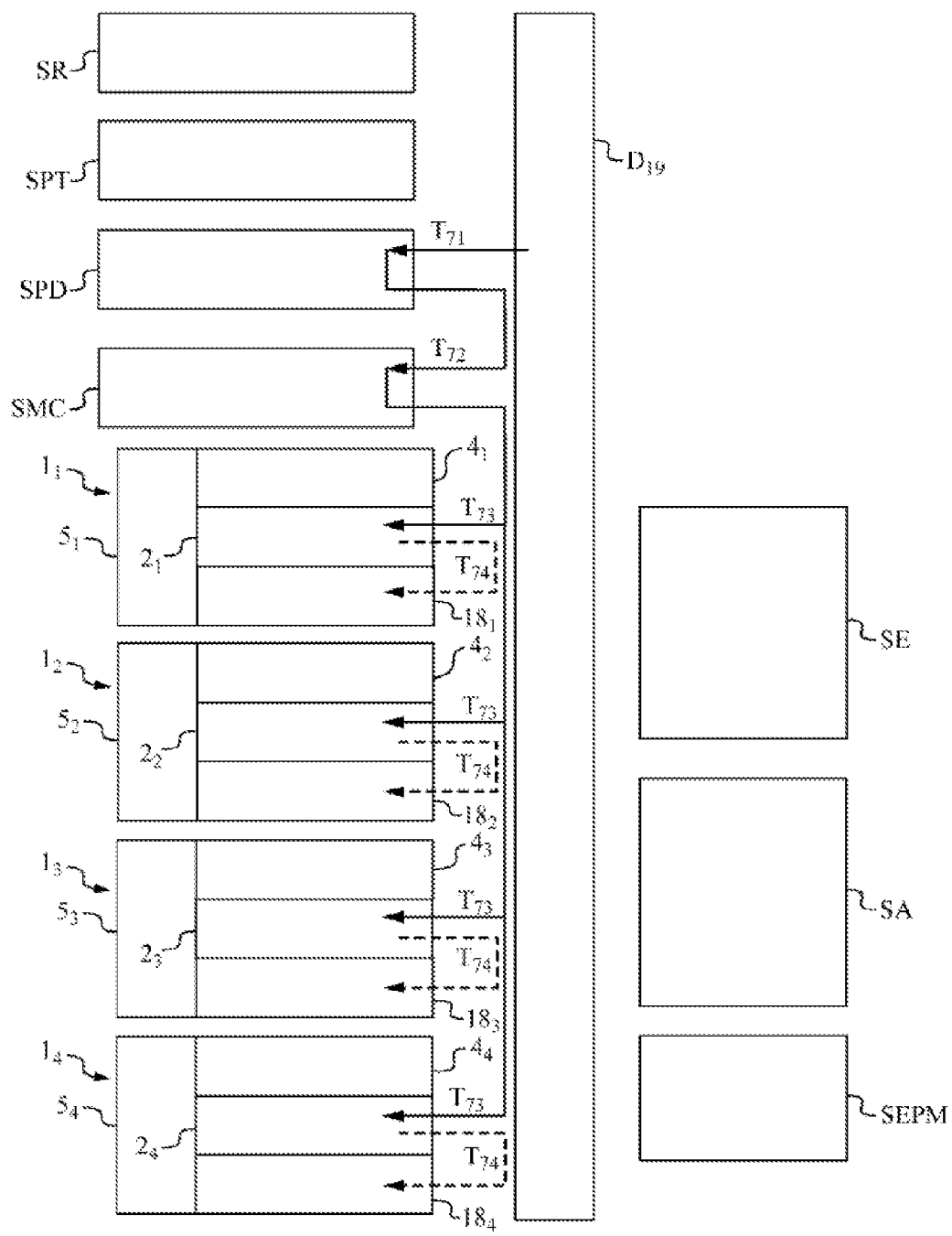
Figure 8:
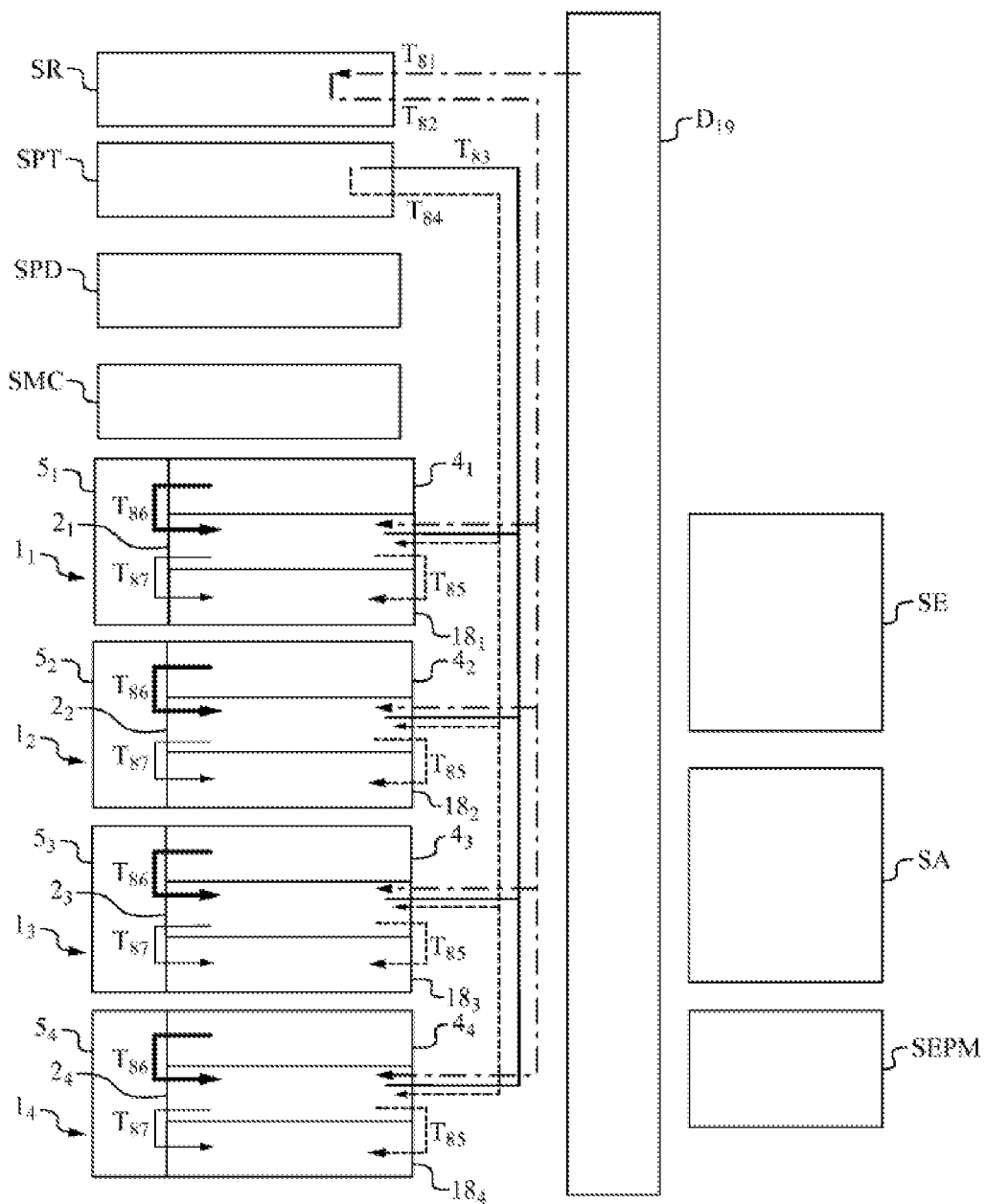

FIGS. 6 to 10 each diagrammatically represent an operating plan for a continuous cell culture method according to the invention, in a closed container (not shown) using any culture support, each figure corresponding to specific stages of the operation, FIG. 7 representing the initial stages of a cell culture;

FIG. 8 representing stages of changing a culture vessel; and

Figure 9:
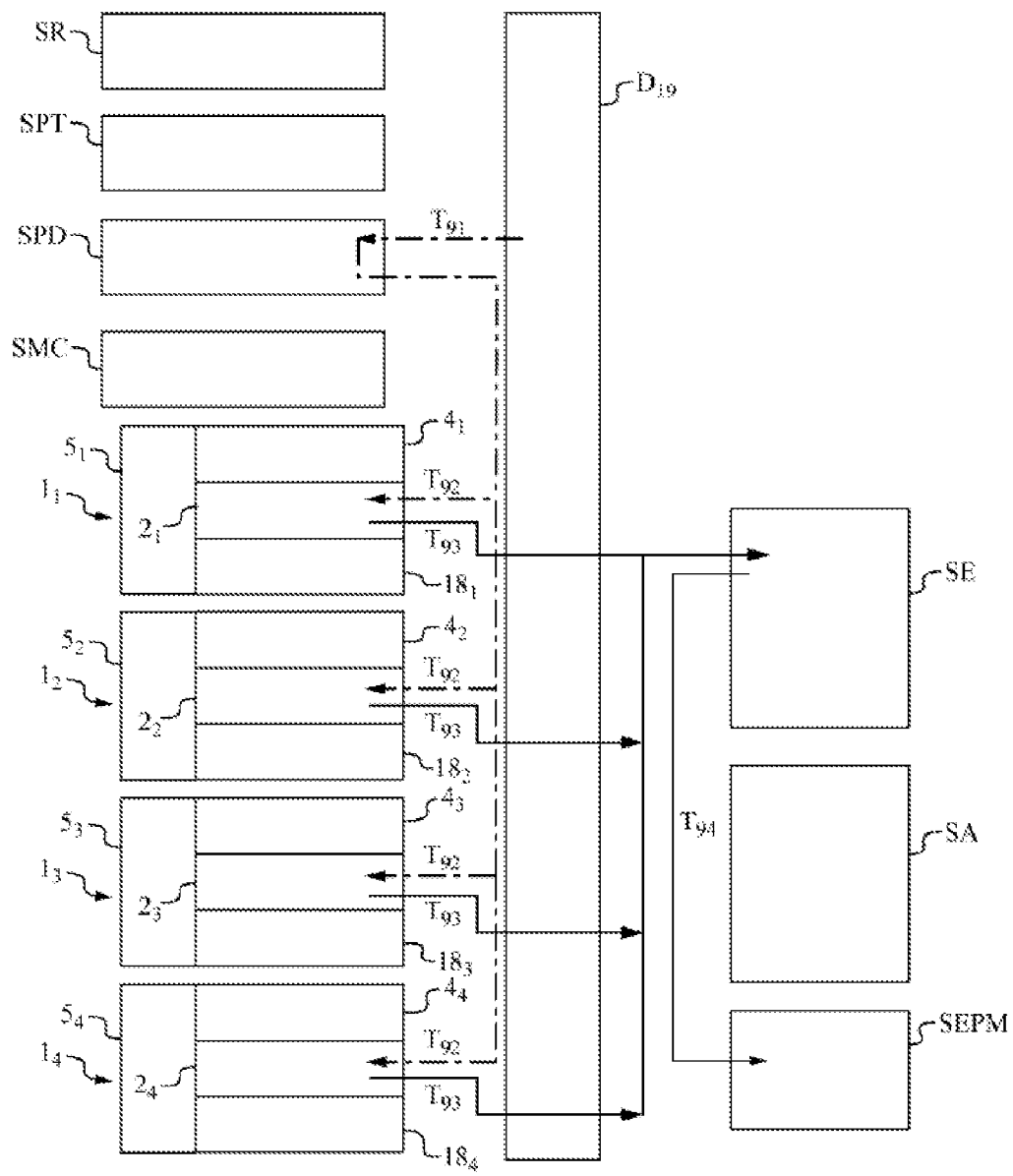

FIG. 9 representing stages of taking samples of culture medium; and

Figure 10:
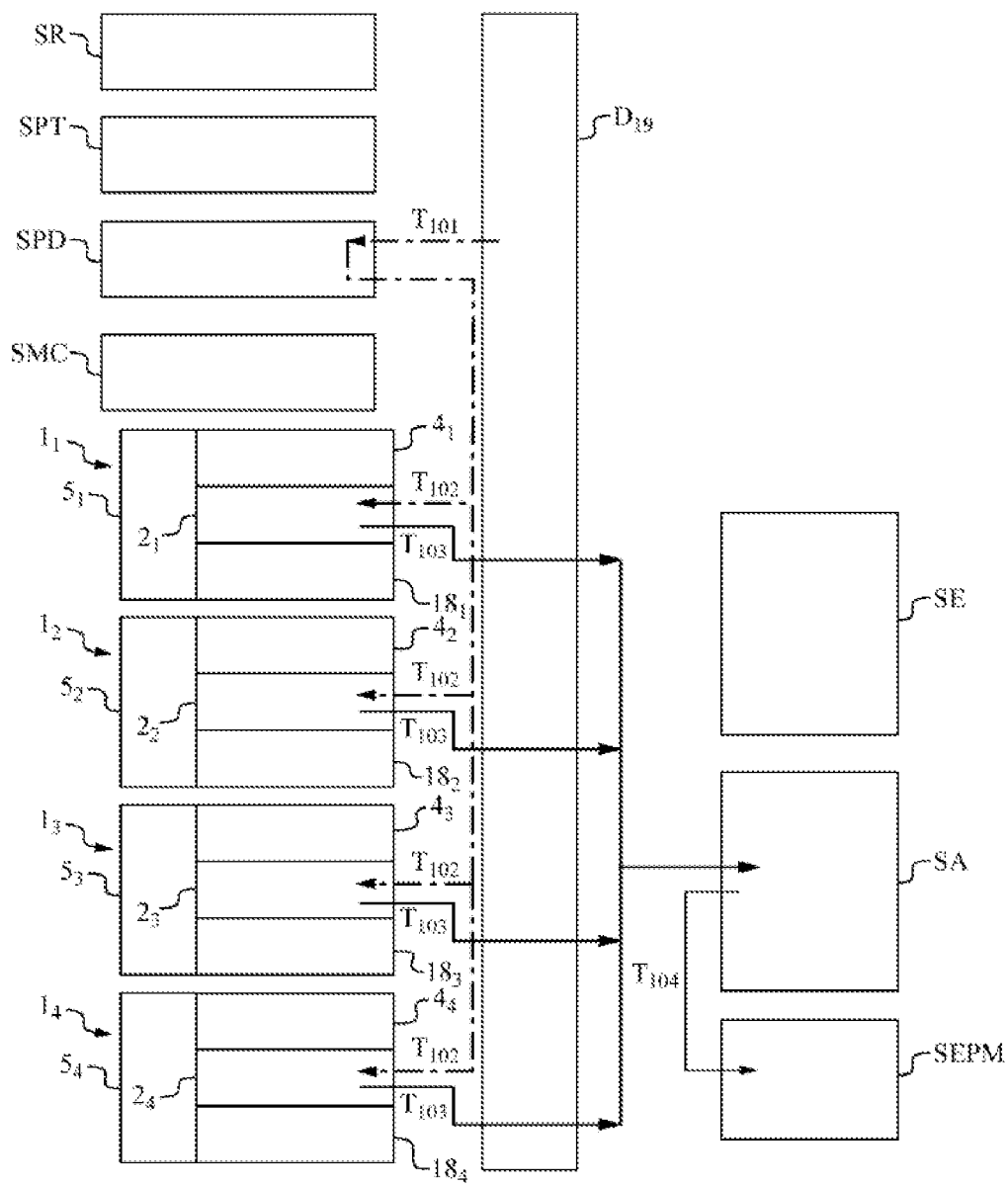

FIG. 10 representing stages of taking micro-samples for analysis.

Figure 1:
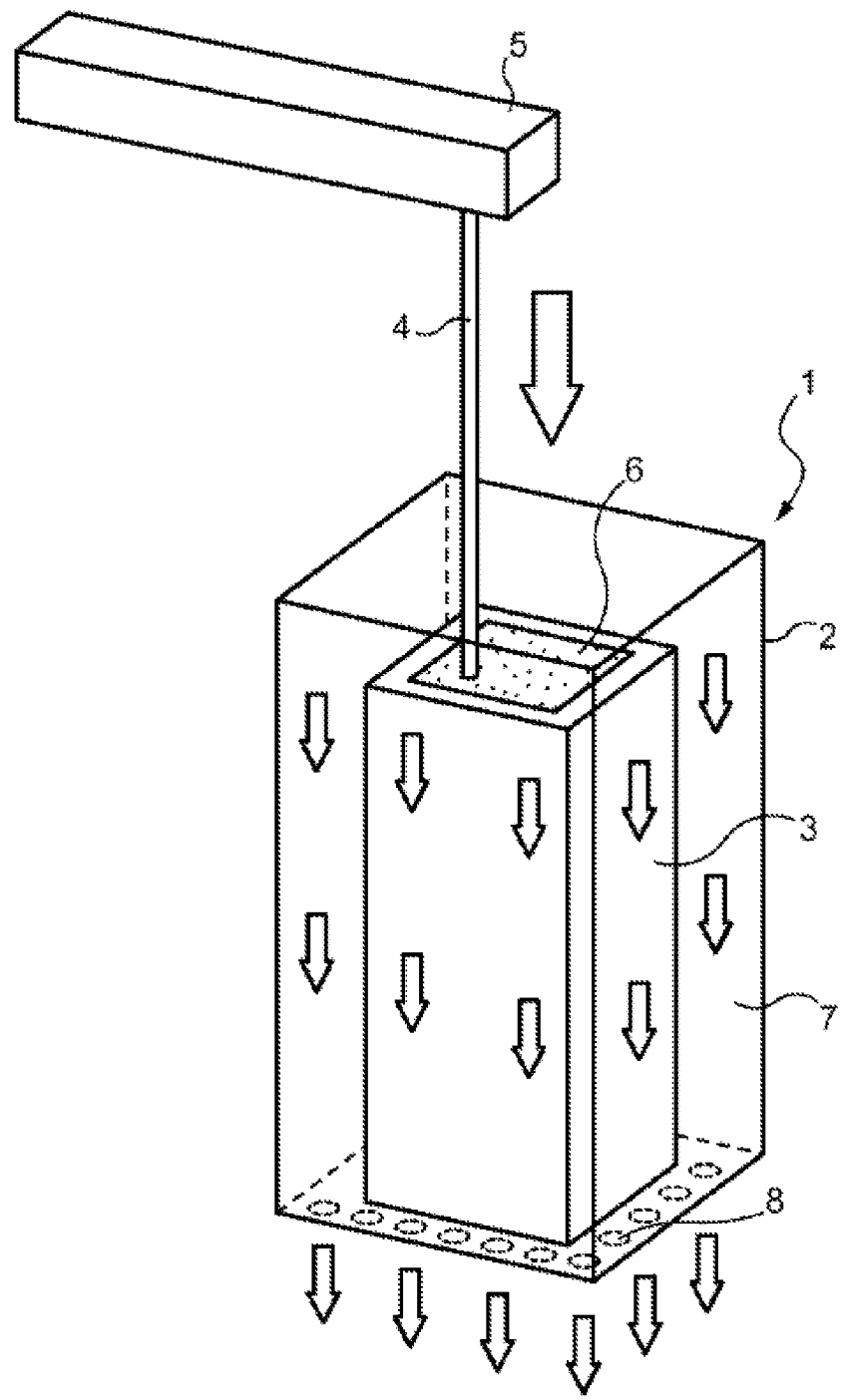

FIG. 1 diagrammatically represents a first culture support 1 according to the invention, open towards the top, suitable for containing a liquid culture medium.

The support 1 comprises a culture vessel 6 housed in a containment tank 2 open towards the top, in which said culture vessel is housed. The culture vessel is placed in a thermostatically controlled case 3, which is optional according to the invention.

The culture medium (shown as filling—dotted—in FIG. 1) is capable of being fed with gas, for example with air, most often under pressure, by a bubbling device constituted here by an aeration rod 4 in the form for example of a bubbling pipe. This rod 4, held using an arm 5 dips vertically into the culture vessel 6 containing the culture medium, through the opening of the culture vessel 6. The arm 5 can carry out a vertical movement in order to position the lower end of the rod 4 at the desired point in the culture vessel 6.

The hollow arrows directed downwards in FIG. 1 represent the sterile gas stream, which is for example sterile air, which passes from the top to the bottom and which passes through the space, or volume, 7 situated between the inner wall of the containment tank 2 and the thermostatically controlled case 3. The sterile gas stream is evacuated through several discharge openings 8. The discharge openings 8 represent a means for extracting the gas stream, and are situated in the lower part, preferably at the bottom, of the containment tank 2.

The culture vessel 6 can consist of any type of vessel open towards the top, of the vial, bottle or Erlen flask type. It is preferable for the culture vessel 6 to be able to be easily positioned and withdrawn from the containment tank 2. As shown in FIG. 1, it is advantageous to choose a culture vessel 6 which does not exceed the walls of the containment tank 2 in height.

The sterile gas stream the circulation of which can be organized from the top to the bottom of the culture support 1, is designed to create an aseptic barrier around the opening of the culture vessel 6, delimited by the inner walls of the containment tank 2.

This gas stream can be activated by creating a partial vacuum in the lower part of the containment tank 2, for example by connecting the discharge openings 8 to a means for aspirating.

The lower part of the containment tank 2 is preferably designed to be embedded in a base provided with additional means for extracting said sterile gas stream, such as a pipe connected to a vacuum pump. If appropriate, said base can be provided with one or more means for collecting or distributing the gas stream, which are useful for the implementation of the method for culture in continuous mode.

Figure 2:
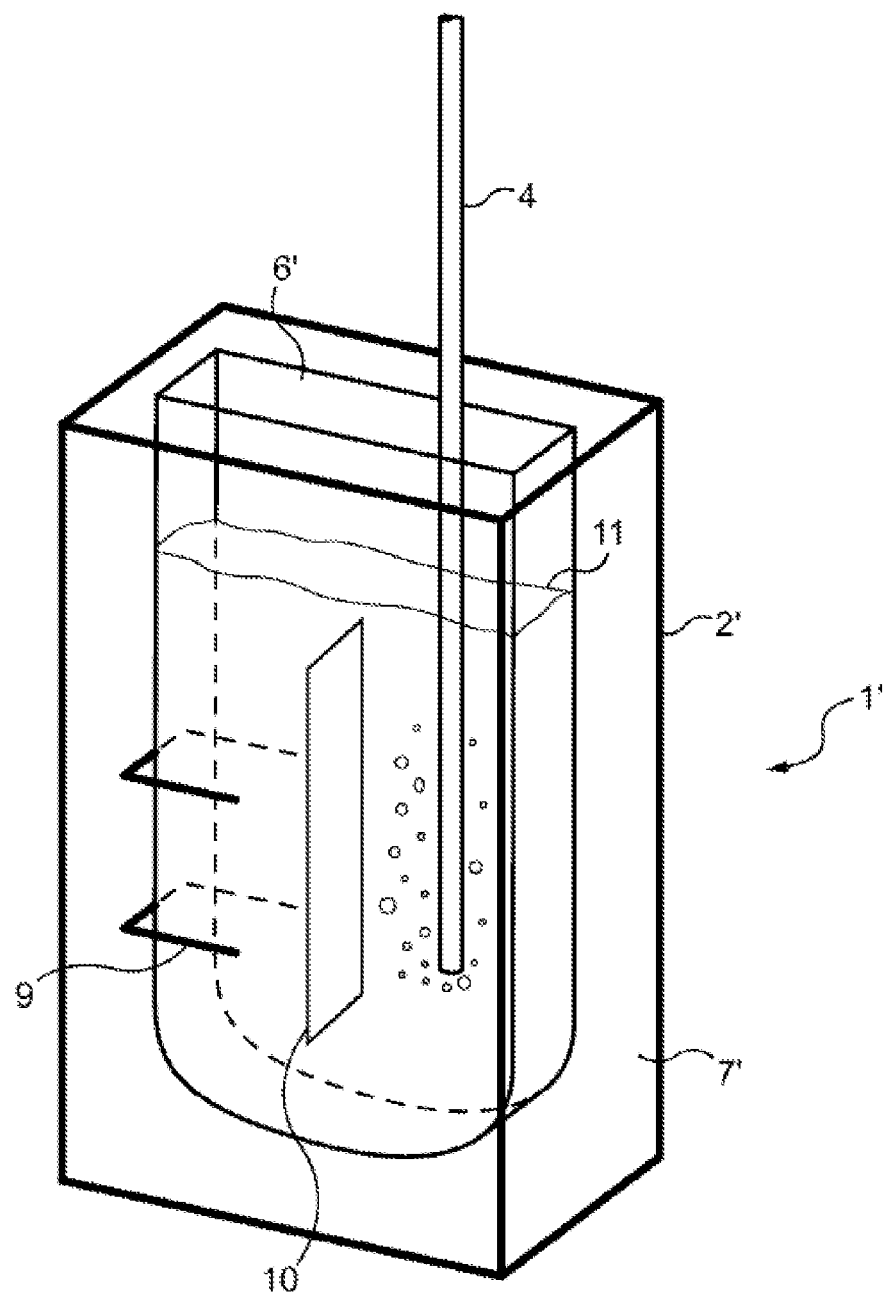

FIG. 2 diagrammatically represents a second culture support according to the invention, 1', in perspective.

The culture support 1' comprises a culture vessel 6' which is present in a containment tank 2', shown transparent here. The culture vessel 6' and the containment tank 2' are both open towards the top. The culture vessel 6' can be easily positioned and withdrawn from the containment tank 2', as it does not exceed the walls of the containment tank 2' in height. The culture vessel 6' comprises a culture medium 11.

A space 7' is defined between the culture vessel 6' and the inner walls of the containment tank 2', said volume 7' being able to be passed through by a gas stream from the bottom to the top. The means for discharging said sterile gas stream are not shown here, but they consist of several openings situated in the base of the containment tank 2'.

Two means for optically measuring of the density 9 of the cells present in the culture medium are arranged on either side of the transparent culture vessel 6', and in the space 7'.

Inside the culture vessel 6', there is a vertical inner wall 10. It allows better circulation of the "air lift" gas injected into the culture medium 11 through the aeration rod 4.

Figure 3:
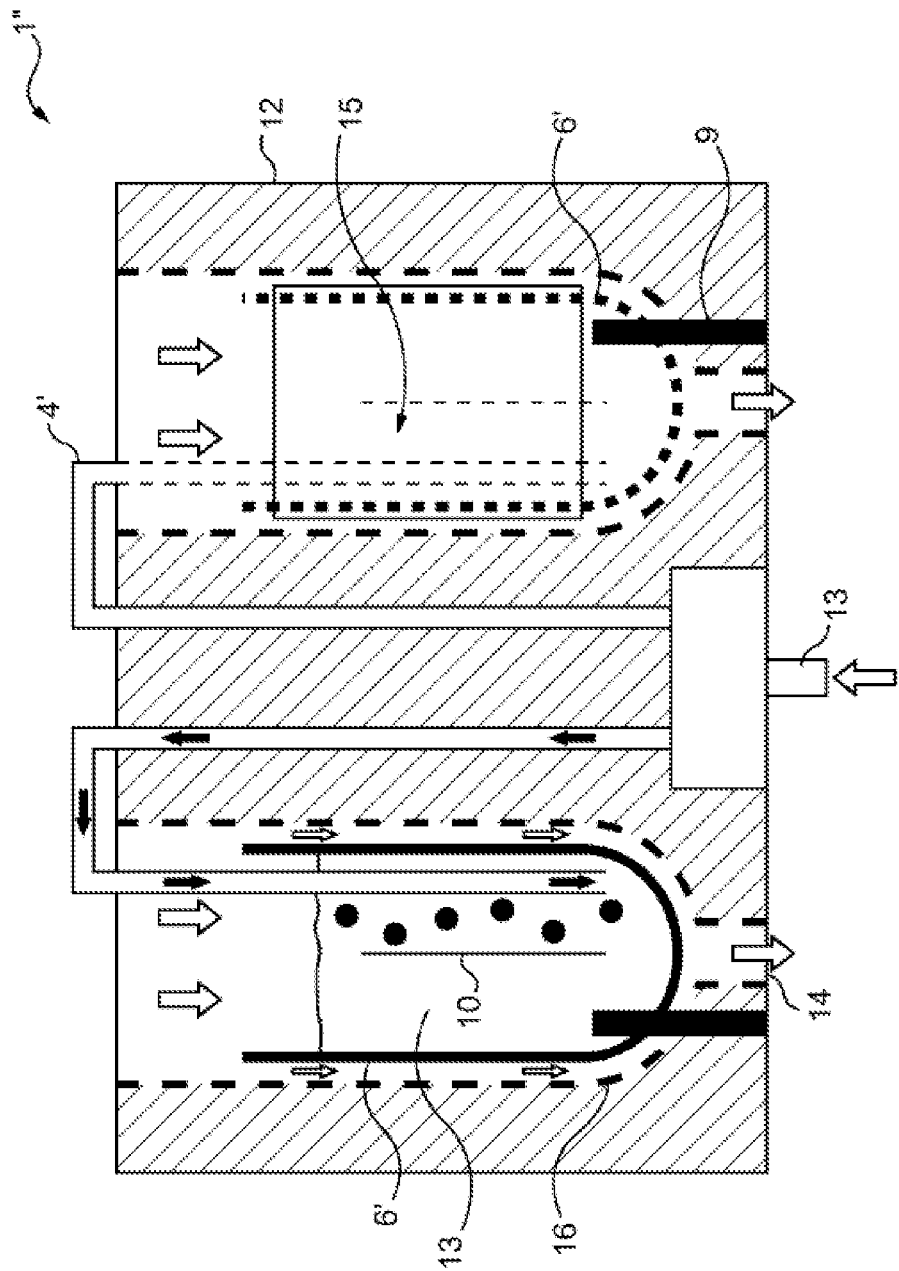
Figure 4:
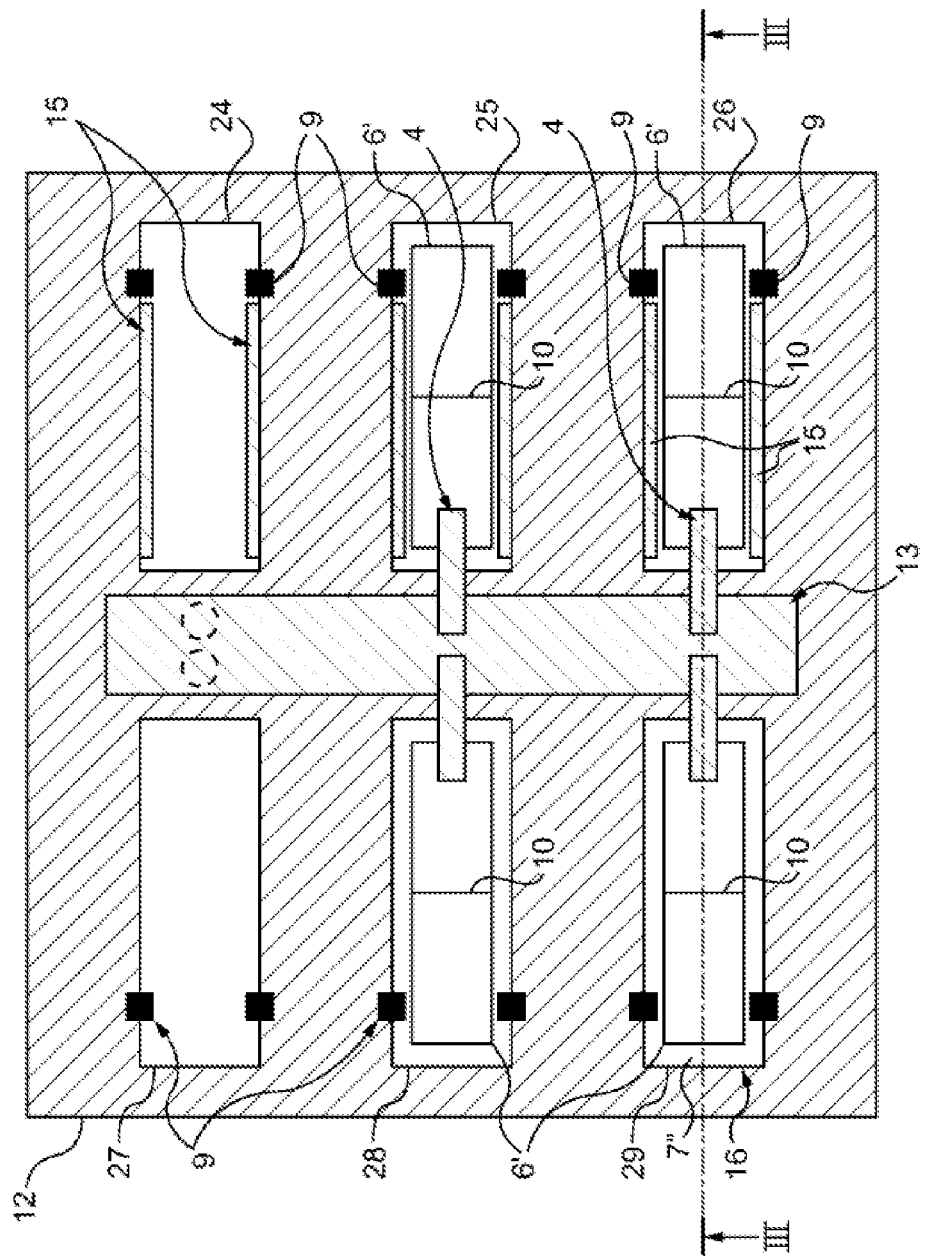
FIG. 4 represents a removable block comprising cells of FIG. 3, viewed from above.

FIGS. 3 and 4 show a preferred culture support 1" according to the invention taking the form of a removable block 12, comprising six cells or compartments 24, 25, 26, 27, 28 and 29, into which containment tanks 16 are inserted. FIG. 4 shows a top view of the block 12, and FIG. 3 shows a cross-section of the block 12 along III-III (cf. FIG. 4).

The block 12 comprises four culture vessels 6', themselves comprising walls 10, and each housed in a cell 25, 26, 28 and 29 of the block 12. Each culture vessel 6' can be placed manually in a cell. The block 12 is preferentially made in one piece. The block 12 is in fact presented as if several culture supports 1' as shown in FIG. 2, and described previously, were attached by the outer wall of their containment tanks 2'. The cells are provided with walls at their periphery forming containment tanks 16.

Gas distribution means, collector and filter contained in an aeration module 13 are extended by individual aeration rods 4 in order to reach each of the culture vessels 6'. The sterile gas stream passing through the culture support 1" from the top to the bottom is represented by hollow arrows, whilst the path of the gas feeding the culture media is represented by solid arrows and bubbles of gas. This sterile gas stream circulation, which is preferably constant, ensures the containment of each culture vessel 6' when the block 12 is placed in a closed container. This culture block 12 can be thermostatically controlled by the presence of heating resistors incorporated in its mass.

The sterile gas stream is evacuated at the bottom of each of the cells comprising a culture vessel 6' by discharge means 14 taking the form of pipes intended to be connected to a means for aspirating the air such as a vacuum pump.

In its lower central part, the block 12 preferentially comprises a manifold collecting and distributing the aeration gas or gases. These gases are conveyed inside each culture vessel 6' by means of a removable elbow pipe 4, ending in aeration rod 4 at the end which dips in the culture vessel 6', and which can be positioned manually on the distribution manifold at the level of connectors, after the installation of the culture vessels 6'. These elbow pipes bring the gas into each culture vessel 6' at a low position in order to cause an "air lift" intended to ensure the supply of oxygen, carbon dioxide or other gas(es) into the culture medium and to ensure a homogeneous mixture of the culture medium.

Luminous side panels, or illuminating plates, 15, are arranged in two cells 25 and 26, laterally, in order to allow the culture of photosynthetic microorganisms. The plates 15 are preferably removable and are light-producing panels allowing the culture of photosynthetic microorganisms, and are situated in the space between the culture vessel 6' and the inner walls of the containment tank 16, or enclosed in one of the walls of the containment tank 16. Preferably, the light is produced using light-emitting diodes (LEDs), the wavelength of which is chosen as a function of the photosynthetic pigments of the microorganisms concerned.

The light emitted can correspond to white light or to lights of different wavelengths depending on the type of LED used. Furthermore, a stroboscopic lighting system can be produced depending on to the method of operation of the LEDs. These lighting possibilities allow the culture of photosynthetic microorganisms such as prokaryotic or eukaryotic microalgae, more particularly in autotrophic mode, in particular by combining lighting and the use of CO2 in the aeration and mixing gases introduced into the cultures.

By autotrophic mode, is meant a culture in which the cells produce organic matter by the reduction of inorganic matter, for example in the form of carbon dioxide, and by taking mineral salts from the medium. The energy necessary for this synthesis comes from the light, as in the case for example of photosynthesis.

The culture support according to the invention therefore makes it possible, if appropriate, to illuminate the cells continuously at each of the stages of the method according to the invention.

According to a variant not shown, the means for producing light can also take the form of a panel forming all or part of one of the walls of the containment tank.

According to a particular aspect of the invention, the means for producing light consist of UV lamps or diodes, the function of which is either to decontaminate the internal volume of the containment tank by irradiation before or after use, or to generate mutations on the cells in culture during the selection process.

Means of optical measurement 9, which are instruments for measuring the turbidity of the culture medium, are inserted, in pairs, into the lower part of each of the cells 24, 25, 26, 27, 28 and 29 in order to monitor changes in the cell density of the culture media present in these cells.

The culture supports in the form of blocks 12 described above offer the advantage of facilitating the implementation of the continuous culture method according to the invention. In fact, several culture vessels 6' can be prepared and placed in a sterile container before the start of the operations. The connection of the distribution manifold to the gas supply system inside the container is done by rapid coupling at the time of the positioning of a block on a base specific to the culture device according to the invention, which can moreover receive several of these blocks. Similarly, it is provided that the necessary electrical connections (heating, detectors, lighting) are made during the placing of a block on a base by simple connection. Such a block facilitates preparatory handling and consequently makes it possible to reduce the automated movements which are carried out inside the closed container during the implementation of the culture method. The device can then operate autonomously over a longer period.

According to a preferred embodiment of the invention, the culture device is an automated device which can comprise a number of six-container removable blocks 12 which can vary from one to 100. Each of the blocks 12 is conditioned manually, sterilized then introduced into the automatic device on a base provided for this purpose. When the blocks 12 are installed, the selective culture method can start by the filling of a culture vessel, its inoculation, then the carrying out of a continuous culture with a constant volume according to the method already described. It is thus possible to carry out a large number of continuous cultures in parallel, each block 12 being able to be the site of an independent experiment.

When a culture needs to be transferred, for example because the accumulation of static variants is becoming too great, a volume of culture in a first culture vessel of the block 12 is pipetted and transferred into a second culture vessel in the same block. When all the culture vessels in a block 12 have been used, the culture can be transferred into a culture vessel in another available block 12, and when completely used the block can be replaced by a new block prepared and equipped with six new sterile culture vessels.

The use of the device provided with culture supports in the form of blocks moreover makes it possible to simplify the robotic functions of pipetting, dilution and transfer.

A device according to the invention can carry out the selective culture of a single microbial species or of a given microbial consortium in ten, twenty or at least forty blocks, i.e. 60, 120 or at least 240 containers simultaneously in order to reach a total culture volume which can reach 1200, 2400 or at least 4800 mL. In this way the probability of obtaining a given mutant is proportionally increased. This increase is particularly useful for cells with a complex genome or for those of species with slow growth.

Figure 5:
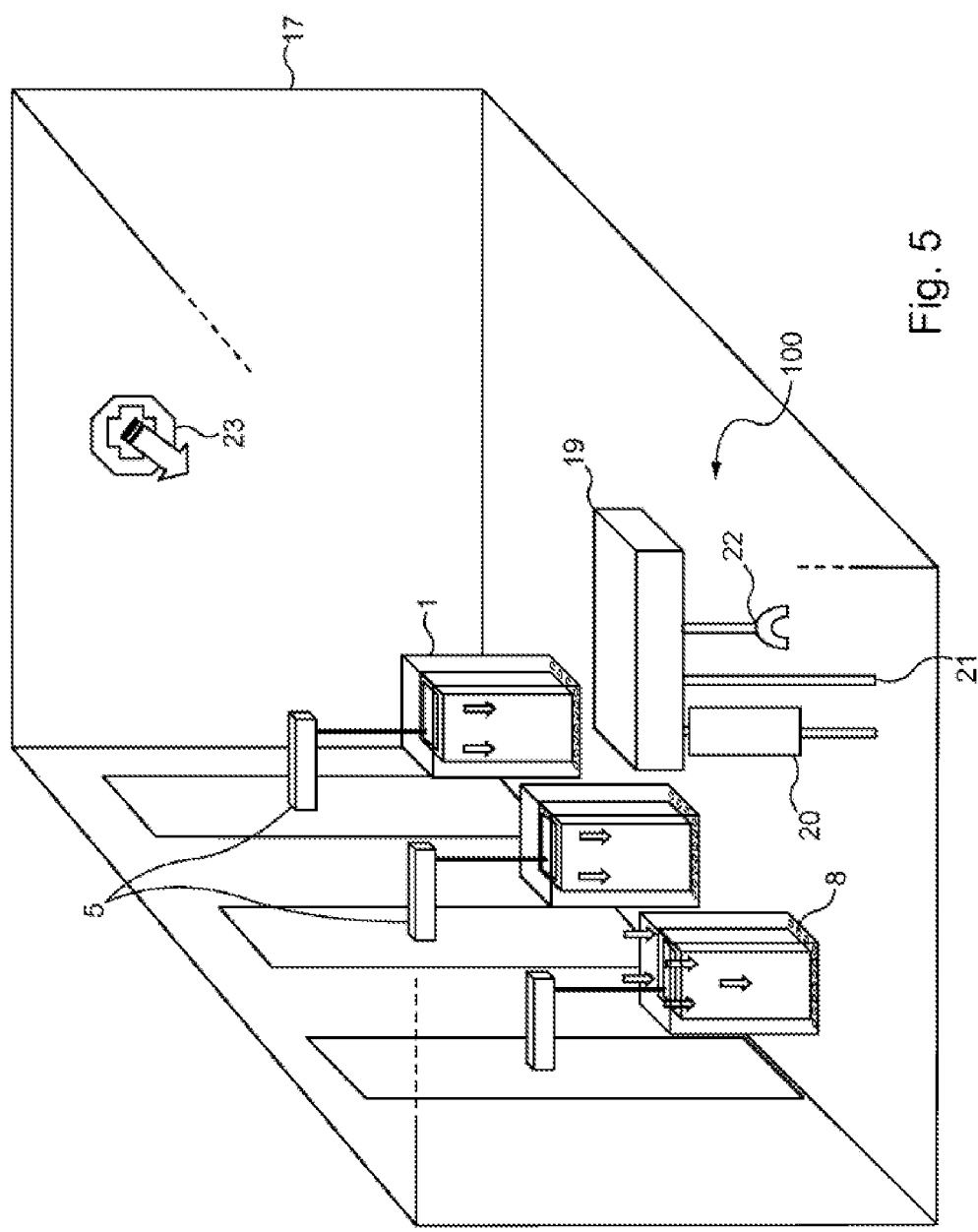
FIG. 5 represents diagrammatically and partially a cell culture device according to the invention, in perspective.

FIG. 5 shows a continuous culture device 100 according to the invention. A container 17, which is closed when the device 100 is in operation, is suggested but not shown fully.

The device 100 comprises several culture supports 1, as shown in FIG. 1, the container 17 and a means for generating a sterile gas stream 23 passing through said container 17. The culture supports 1 operate in parallel in the container 17. The container 17 is passed through by a robotic arm 19 mounted on a rail, capable of moving in the three spatial dimensions. This robotic arm 19 is equipped with a transfer pipette 20 allowing the replenishment of the culture medium, a dilution pipette 21 and handling clamp 22.

The size of the container 17 is not limited, which allows several cultures to be carried out simultaneously in several identical or different culture supports 1, placed in the same container 17.

The sterile gas stream which passes through the container 17 is represented by hollow arrows from the means 23 located at the top of the container 17 so that said sterile gas stream is directed from the top to the bottom of the culture support 1. The sterile gas stream which passes through the container 17 is evacuated out of the container 17 through openings 8 situated in the base of the culture supports 1.

Preferably the means for extracting the sterile gas stream is designed so as to create a partial vacuum in the space situated between the culture vessel 1 and the containment tank 2 of the same culture support 18. It is generally associated with a gas stream extraction means suitable for aspirating the gas stream surrounding the periphery of the opening of the culture vessel, such as a vacuum pump (not shown) situated, for example, under the floor of the container 17.

FIGS. 6 to 10 each represent diagrammatically an operating plan of a continuous cell culture method according to the invention, in a closed container (not shown) using any culture support, each figure corresponding to a block diagram explaining specific stages of the operation, FIG. 7 representing the initial stages of a cell culture;

FIG. 8 representing stages of changing a culture vessel; and

FIG. 9 representing stages of taking culture medium samples; and

FIG. 10 representing stages of taking micro-samples for analysis.

FIGS. 6 to 10 are described in the following examples.

The purpose of the following examples is to describe the operation of an automatic culture device according to the invention designated "BED". This is a preferred device according to the invention which imposes no limitation on the invention claimed in the present application.

EXAMPLES

The operating plan of a continuous cell culture method according to the invention, in a closed container (not shown) uses any culture support, rather the type of culture support, each figure corresponding to a block diagram explaining specific stages of the operation of a continuous culture device according to the invention, in a version comprising:

four culture supports $1_1$, $1_2$, $1_3$ and $1_4$ each comprising a single containment tank $2_1$, $2_2$, $2_3$ and $2_4$ and a single culture vessel $6'_1$, $6'_2$, $6'_3$ and $6'_4$. Each culture support is equipped with a bubbler arm $5_1$, $5_2$, $5_3$ and $5_4$, intended to be connected to a sterile aeration rod (or bubbling pipe), a stock of aeration rods $4_1$, $4_2$, $4_3$ and $4_4$ (not shown), and with an airlock for ejection from the culture vessel $18_1$, $18_2$, $18_3$ and $18_4$, It is possible, in a variant, to consider that the references $1_1$, $1_2$, $1_3$ and $1_4$ represent culture blocks of the removable block type 12 comprising several (for example two, four, six etc.) culture vessels.

a reserve (or stock) of sterile culture vessels SR, a reserve (or stock) of transfer pipettes SPT, a reserve (or stock) of dilution pipettes SPD for adding fresh culture medium, a stock of diluent medium SMCD or of sterile culture medium, a sampling airlock SE for taking samples out of the container, an airlock for ejection of the pipettes and contaminated equipment SEPM, An analysis station airlock SA allowing the introduction of equipment or reagents etc. for carrying out measurements, a multifunctional articulated arm passing through the container over the length and the perimeter of movement, in three dimensions, of the arm being marked by the zone $D_{19}$;

The transfer pipettes generally have a volume approaching the volume of a culture vessel, i.e. most often 20 to 30 mL, and are intended to transport most of the culture medium from one culture vessel to another. The dilution pipettes for their part generally have a much smaller volume, for example most often from 2 to 3 mL.

The arrows and the references of the type $T_{xy}$, where x is the number of the Figure and y the number of the path for said Figure, indicate the course of the articulated arm at the start of the culture (FIG. 6), during a dilution operation (FIG. 7), during an operation of changing a culture vessel (FIG. 8), during an operation of taking a culture sample (FIG. 9), and during an operation of taking a culture sample for analysis inside the closed container (FIG. 10).

Operation of the BED Device

Basic Operating Cycle

1) Initial Stages of a Culture

The operator installs the following loaders/racks in the container of the device, in the respective storage areas:

Sterile culture tanks (or culture vessels),

Sterile transfer pipettes,

Sterile dilution pipettes,

The sterile bubbling pipes or aeration rods intended to be linked to the bubbler arms $5_1$, $5_2$, $5_3$ and $5_4$, The operator installs the closed sterile reservoirs containing the different diluents in the cell culture device, in the respective storage areas.

The operator opens the reservoirs containing the different diluents.

The operator installs the closed sterile culture vessel containing the pure culture no. 1 in the robot in the dedicated position.

The operator opens said culture vessel.

The multifunctional automated articulated arm grips a tank from its rack in the stock SR (FIG. 6, path 1 $T_{61}$), and conveys it up to the culture support dedicated to this culture (FIG. 6, path 2 $T_{62}$). In the case shown in FIG. 6, the first culture support $1_1$ is filled with pure culture no. 1 in a culture tank or vessel $6'_1$, then successively, as explained hereafter, the other three culture supports $1_2$, $1_3$ and $1_4$ are filled with a culture medium, by transfer using a transfer pipette from a culture support into the corresponding culture tank or vessel $6'_2$, $6'_3$ and $6'_4$.

The multifunctional automated articulated arm pierces the protective film of the culture vessel (sterile tanks).

The multifunctional automated articulated arm takes a transfer pipette from its rack in the stock SPT (FIG. 6, path 3 $T_{63}$).

The multifunctional automated articulated arm, equipped with a transfer pipette, takes a sample of the culture from the tube containing the culture (FIG. 6, path 4 $T_{64}$).

The multifunctional automated articulated arm conveys the culture up to the corresponding support and empties the transfer pipette into the culture vessel (FIG. 6, path 5 $T_{65}$).

The automated articulated bubbler arm takes a sterile bubbling pipe, then positions the sterile bubbling pipe in the culture vessel (FIG. 6, path 6 $T_{66}$). The automated articulated bubbler arm opens the gas supply.

2) Continuous Culture System

The automatic device receives the triggering signal given by the detector situated in the culture support. The latter is programmed to monitor a physicochemical parameter and to transmit a signal when a critical value of this parameter is reached.

The automated articulated arm then takes a sterile dilution pipette from the corresponding stock SPD (FIG. 7, path 1 $T_{71}$).

The automated articulated arm takes a specific volume of a diluent No. 1 then takes a bubble of sterile air in order to maintain sterilization during the conveying (FIG. 7, path 2 $T_{72}$).

The automated articulated arm recommences this operation n times in order to take the desired volume of n diluents.

The multifunctional automated articulated arm conveys the dilution pipette up to the corresponding support and empties the dilution pipette into the culture tank (FIG. 7, path 3 $T_{73}$).

The multifunctional automated articulated arm positions the dilution pipette for the discharge of the surplus volume.

The multifunctional automated articulated arm evacuates the surplus volume, 2 methods of discharge are possible:

a) either the multifunctional automated articulated arm positions the dilution pipette in the culture and takes a specific volume of culture then sucks up a bubble of air, or b) the multifunctional automated articulated arm positions the dilution pipette at a specific height in the culture container (corresponding to the desired volume of culture) and sucks up the entire excess volume of culture then sucks up a bubble of air.

The multifunctional automated articulated arm conveys the dilution pipette containing the surplus culture above the ejection airlock which acts as the liquid discharge station/nearest waste bin (for maintaining sterilization) and empties the content of the dilution pipette into said ejection airlock $18_1$, $18_2$, $18_3$ or $18_4$ (FIG. 7, path 4 $T_{74}$)

Similarly, the multifunctional automated articulated arm conveys the empty dilution pipette above the ejection airlock which acts as the solid discharge station/nearest waste bin (for maintaining sterilization) and ejects the dilution pipette into said ejection airlock $18_1$, $18_2$, $18_3$ or $18_4$ (FIG. 7, path 4 $T_{74}$).

3) Tank Replacement

The automatic device detects the signal triggering a change of culture vessel either at the end of a specific cycle time or following the detection of a biofilm.

The multifunctional automated articulated arm grips a tank from its rack in the stock SR and conveys it up to the temporary position dedicated to this culture (FIG. 8, paths 1 and 2 $T_{81}$ and $T_{82}$).

The automated articulated arm takes a sterile transfer pipette from the reservoir SPT (FIG. 8, path 3 $T_{83}$)

The automated articulated bubbler arm closes the gas supply and takes the used bubbling pipe from the culture.

The automated articulated bubbler arm ejects the used bubbling pipe into the ejection airlock which acts as the solid discharge station/nearest waste bin (for maintaining sterilization) and ejects the used pipe into said ejection airlock $18_1$, $18_2$, $18_3$ or $18_4$.

The automated articulated arm takes a sample of the culture.

The multifunctional automated articulated arm conveys the transfer pipette containing the culture up to the new tank in the temporary position dedicated to this culture and empties the transfer pipette into the new culture tank (FIG. 8, path 4 $T_{84}$).

The multifunctional automated articulated arm conveys the empty transfer pipette above the ejection airlock which acts as the solid discharge station/nearest waste bin (for maintaining sterilization) and ejects the transfer pipette into said ejection airlock $18_1$, $18_2$, $18_3$ or $18_4$ (FIG. 7, path 4 $T_{74}$) (FIG. 8, path 5 $T_{85}$).

The automated articulated bubbler arm takes a sterile bubbling pipe (FIG. 8, path 6 $T_{86}$).

The automated articulated bubbler arm positions the sterile bubbling pipe in the culture tank.

The automated articulated bubbler arm opens the gas supply.

The culture vessel is ejected via the ejection airlock (FIG. 8, path 7 $T_{87}$).

4) Selection of Microorganisms Developing in Suspension:

The cultures are carried out in a culture vessel (disposable plastic tanks) in a culture support as shown in FIG. 1.

This disposable culture vessel can be regularly replaced, when necessary (development of biofilm) by a new sterile vessel via the action of a robotic arm, as described above.

An overview of the culture device is for example given in FIG. 5.

During a change of tank, the arm ensures the pumping of the medium into a sterile pipette during the exchange the culture tanks, then replaces the culture medium in the new sterile tank (container-exchange function).

This robotic arm also performs the function of pipetting a portion of the culture and replacing the removed volume with the same volume of fresh medium (dilution function), the frequency of dilution can be set by the experimenter (chemostat) or controlled by the cell density of the culture (turbidostat).

Any physical object coming into contact with the culture (aeration tube, transfer pipette, dilution cones) is replaced after each use by a new sterile object.

The container (=the culture tank) is placed in a thermostatically controlled metal case making it possible to keep the culture at a controlled temperature. This case is equipped with one or more instruments (transmitter/receiver at different wavelengths) making it possible to measure the cell density (visible, IR) in the tank, as well as the concentration of certain absorbent molecules.

The culture tank and the thermostatically controlled case are situated in a containment tank inside which a sterile gas stream, for example of sterile air, flows constantly around the case and the tank so as to achieve a constant sterile containment of the latter (see FIG. 1).

In this way, only the organisms developing in suspensive mode (and therefore subjected to the dilution) are maintained in growth over the long term under selective conditions.

Due to the use of disposable single-use tanks and accessories and the absence of complex fluidic systems, the system does not require any complex and time-consuming sterilization operations.

All the tanks in place in the system are functional and ensure the development of selective cultures.

Moreover, the system makes it possible to control the culture either with respect to a constant degree of dilution and constant volume with compensation for evaporation, or with respect to a variable degree of dilution without compensation for evaporation, or with respect to a variable degree of dilution with compensation for evaporation.

The possibility of finely controlled molecular supplies in liquid phase via the action of the robotic arm, makes it possible to envisage the precise change of the selection pressures applied to the cultures for a large number of constituents without requiring the multiplication of dedicated branches of the fluidic system.

Moreover, the addition of products which are difficult to handle (such as for example acetaldehyde which is volatile and reactive) is possible without having to pass this product through a complex fluidic system.

Furthermore, the system makes it possible to envisage the addition of solid particles such as cells immobilized in alginate beads, liquids immiscible with water and various additives which are impossible to convey practically in aqueous phase in a complex fluidic system.

Moreover, aliquots of low volume can be taken via the robotic arm in a sterile manner at any time during the culture in order to be transferred to any type of analytic equipment (HPLC, PCR, ELISA, MS etc.) which is external to the BED system and the results of which can be integrated for the control of the culture in progress.

Moreover, the system makes it possible to use different forms of culture tanks depending on the requirements for culture of the microorganisms.

5) Selection of Microorganisms Developing in the Form of Biofilms

The device described previously allows the addition of plates of different materials to the culture tank via the robotic arm for the selection of cells developing in the form of biofilms.

The fraction of the culture that adheres to these plates, can be preserved whilst the culture medium containing the cells in suspension is withdrawn and replaced with fresh medium. Similarly, the plates covered with biofilms can be moved into a new sterile culture vessel using the robotic arm.

In this way, it is possible to select cell variants which develop the ability to adhere to a support or to aggregate in order to form structures such as biofilms.

Optional Additional Operations

1) Addition of a Reagent

All types of reagents can be considered in this context for example chemical products of the biochemical products (proteins, DNA etc.), biological products (cell suspensions) etc.

The robot detects the signal triggering the addition of a reagent.

The automated articulated arm takes a micropipette of sterile reagent.

The automated articulated arm conveys the micropipette of sterile reagent up to the stock containing the desired reagent.

The automated articulated arm takes a negligible volume of the reagent compared to the specific total volume of culture (for example 25 μL of reagent) then takes a bubble of sterile air.

The multifunctional automated articulated arm conveys the micropipette containing the reagent up to the corresponding incubator and empties the dilution pipette into the culture tank.

The multifunctional automated articulated arm rinses the wall of the micropipette by a suction and discharge cycle in the micropipette.

The multifunctional automated articulated arm conveys the micropipette of reagent above the station for discharge of solid elements/waste bin and ejects reagent from the micropipette into the station for discharge of solid elements.

2) Routine Sampling

The operator installs a sterile tube in the sampling or aliquoting station SE.

The operator opens the sterile tube in the sampling or aliquoting station SE.

The robot detects the signal triggering a dilution and the signal triggering a sampling operation.

The robot carries out a dilution as described in the section preceding paragraph 2) apart from one stage: the multifunctional automated articulated arm conveys the dilution pipette containing the surplus culture above the station SE and deposits the content of the dilution pipette in the open sterile tube (FIG. 9, path 3 $T_{94}$).

The operator re-closes the sterile tube in the station SE.

The operator re-closes the sampling tube and recovers the culture medium via the sampling airlock SE.

3) Emergency Sampling

The operator installs a sterile tube in the sampling station SE.

The operator opens the sterile tube in the sampling station SE.

The robot detects the signal triggering a sampling operation.

The automated articulated arm takes a sterile dilution pipette from the stock SPD (FIG. 9, path 1 $T_{91}$).

The automated articulated arm conveys the sterile dilution pipette up to the culture concerned (FIG. 9, path 2 $T_{92}$).

The automated articulated arm takes a specific volume (for example 2 mL) of culture then a bubble of air.

The multifunctional automated articulated arm conveys the dilution pipette containing the sample of culture above the sampling station and deposits the contents of the dilution pipette in the open sterile tube (FIG. 9, path 3 $T_{93}$).

The multifunctional automated articulated arm conveys the used dilution pipette above the station for discharge of solid elements/waste bin and ejects the dilution pipette into the station for discharge of solid elements (FIG. 9, path 4 $T_{94}$).

The operator re-closes the sterile tube in the sampling station.

The operator re-closes the sampling tube and recovers the aliquot of the culture.

4°) Taking a Micro-Sample for Analysis

The robot detects the signal triggering the taking of one micro-sample for analysis.

The automated articulated arm takes a sterile micropipette from the stock SEPD (FIG. 10, path 1 $T_{101}$).

The automated articulated arm conveys the sterile micropipette up to the culture concerned (FIG. 10, path 2 $T_{102}$).

The automated articulated arm takes a specific micro-volume (for example 10 μL) of culture then a bubble of air.

The multifunctional automated articulated arm conveys the micropipette containing the sample of culture above the analysis station SE and deposits the contents of the micropipette in the position assigned to this sample in the analytic platform (FIG. 10, path 3 $T_{103}$).

The multifunctional automated articulated arm conveys the used micropipette above the airlock for ejection of the pipettes and contaminated equipment SEPM which acts as a station for discharge of solid elements/waste bin and ejects the micropipette into said airlock SEPM (FIG. 10, path 4 $T_{104}$).

The invention claimed is:

1. An automated and remotely controlled continuous cell culture method for selecting variants of an initial inoculum of live cells, which variants are proliferating in suspension, said method comprising the following stages:
   a) seeding one or more live cells in a liquid culture medium contained in a first disposable single-use culture vessel whose top has an opening which is kept open in a closed container, wherein the opening in the top of the culture vessel is sufficiently wide so as to accommodate the introduction of sterile disposable single-use pipettes, gas bubbling device, and optionally, measurement probes, through the opening into the liquid culture medium in the culture vessel;
   b) the cells in said culture medium, which are in suspension, are brought to a specific growth stage, which corresponds to a given cell density or to a physicochemical parameter measured in the culture medium;
   c) the cell density in the culture medium containing the cells in suspension, or the value of said physicochemical parameter, reached in stage b), is kept substantially constant by the automated introduction of fresh culture medium or a diluent into said culture vessel with a sterile disposable single-use pipette, followed by automated disposal of the used pipette;
   d) a portion of the culture medium of the culture obtained in c) containing the cells in suspension is removed by automated pipetting with a sterile disposable single-use pipette so as to maintain constant the volume of the culture, followed by automated disposal of the used pipette;
   e) a fraction of the culture medium containing the cells in suspension obtained in d) is removed by automated transfer with a sterile disposable single-use pipette and is transferred by robotic means into a second disposable single-use culture vessel whose top has an opening which is kept open in the same closed container as the first culture vessel, followed by the automated disposal of the used pipette;

f) said first culture vessel with the remaining culture fraction that it contains is robotically withdrawn and disposed of; and g) after several generations of culture in the second vessel, the cells proliferating in suspension are selected, wherein at least the stages a) to f) are carried out in the closed container.

2. The method according to claim 1, wherein a gas stream, such as sterile air, is applied continuously at the periphery of the openings at the tops of the culture vessels.

3. The method according to claim 1, wherein a sterile gas stream is applied from the top to the bottom of the culture vessels.

4. The method according to claim 3, wherein the sterile gas stream from the top to the bottom is maintained by creating a partial vacuum at the periphery of the culture vessels.

5. The method according to claim 4, wherein the sterile gas stream is discharged out of the container at the bottom of said culture vessels.

6. The method according to claim 1, wherein stages a) to f) are repeated one or more times with successive culture vessels before proceeding with stage g) in which the second culture vessel is the last in the succession of culture vessels.

7. The method according to claim 1, wherein a substantially constant cell density is maintained in the culture in stage c) by diluting the culture with fresh medium while keeping a constant volume of culture medium containing the cells in suspension in the culture vessel.

8. The method according to claim 1, wherein the first used culture vessel is discharged from the closed container using an airlock.

9. The method according to claim 1, wherein the container is thermostatically controlled allowing regulation of the temperature of the cell culture.

10. The method according to claim 1, wherein several cultures are carried out simultaneously in several culture vessels placed in the same container.

11. The method according to claim 1, wherein gas is injected by means of a bubbling device introduced into the culture vessel.

12. The method according to claim 1, wherein several stages of the method are carried out using one or more automated arms allowing movements inside the container.

13. The method according to claim 1, wherein the cells are cultured continuously over a number of generations greater than $10^2$ without opening of the container to the outside environment.

14. The method according to claim 1, wherein the method is applied to the culture of autotrophic microorganisms and said culture is illuminated during the different stages of said method.

15. The method according to claim 1, wherein the cells are cultured continuously over a number of generations greater than $10^6$ generations, without opening of the container to the outside environment.

16. The method according to claim 1, wherein the cells are cultured continuously over a number of generations greater than $10^{10}$ generations, without opening of the container to the outside environment.

17. The method according to claim 1, wherein the live cells are microorganisms.

18. The method according to claim 1, wherein the live cells are bacteria, yeast or unicellular algae.

* * * * *